(12) United States Patent
Haworth et al.

(10) Patent No.: US 8,978,492 B1
(45) Date of Patent: Mar. 17, 2015

(54) SAMPLING CONTAINER AND METHOD OF SAMPLING

(75) Inventors: Jonathan L. Haworth, Hendersonville, TN (US); Cody Curtsinger, Franklin, KY (US); Aaron Holmes, White House, TN (US); Brian Swain, White House, TN (US)

(73) Assignee: Des-Case Corporation, Goodlettsville, TN (US)

( * ) Notice: Subject to any disclaimer, the term of this patent is extended or adjusted under 35 U.S.C. 154(b) by 1070 days.

(21) Appl. No.: 12/763,129

(22) Filed: Apr. 19, 2010

Related U.S. Application Data

(60) Provisional application No. 61/170,610, filed on Apr. 18, 2009, provisional application No. 61/239,856, filed on Sep. 4, 2009.

(51) Int. Cl.
*G01N 1/20* (2006.01)
*G01N 1/14* (2006.01)

(52) U.S. Cl.
USPC .... 73/864.63; 73/291; 73/863.85; 73/863.86; 73/864.34

(58) Field of Classification Search
CPC ........ G01F 23/02; G01N 1/14; G01N 1/2035; G01N 2001/1427; G01N 2001/205; G01N 2001/2071
USPC ............ 73/291, 323, 863.52, 863.57, 863.83, 73/863.85–863.86, 864.34, 864.51, 864.63
See application file for complete search history.

(56) References Cited

U.S. PATENT DOCUMENTS

| | | | | |
|---|---|---|---|---|
| 3,174,345 A | * | 3/1965 | Bodmin | 73/863.51 X |
| 4,271,704 A | * | 6/1981 | Peters | 73/864.63 |
| 4,602,726 A | * | 7/1986 | Goda | 222/321.6 |
| 6,543,302 B1 | * | 4/2003 | Pratt | 73/864.63 |
| 6,736,792 B1 | * | 5/2004 | Liu | 604/94.01 |
| 6,837,120 B2 | * | 1/2005 | Cordry | 73/864.63 X |
| 6,976,398 B2 | * | 12/2005 | Leoncavallo et al. | 73/863.52 |
| 8,402,843 B2 | * | 3/2013 | Nance et al. | 73/864.63 |
| 8,621,944 B2 | * | 1/2014 | Stein | 73/863.85 |
| 8,863,594 B2 | * | 10/2014 | Taylor et al. | G01N 1/14 |
| 2003/0070499 A1 | * | 4/2003 | Pratt | 73/864.63 |
| 2004/0187611 A1 | * | 9/2004 | Leoncavallo et al. | 73/864.63 |
| 2005/0199077 A1 | * | 9/2005 | Prybella et al. | 73/863.86 |
| 2006/0122082 A1 | * | 6/2006 | Paul | 510/130 |
| 2007/0025886 A1 | * | 2/2007 | Yong | 422/102 |

(Continued)

FOREIGN PATENT DOCUMENTS

| | | | | | |
|---|---|---|---|---|---|
| GB | 2071846 A | * | 9/1981 | | 73/863.86 |
| GB | 2197469 A | * | 5/1988 | | 73/863.86 |
| GB | 2236522 A | * | 4/1991 | | 73/864.63 |
| GB | 2258217 A | * | 2/1993 | | 73/863.86 |

(Continued)

OTHER PUBLICATIONS

Vernay Product Information Sheet, Umbrella Check Valve, Part No. 1195-102, Design Reference VA3333, Jun. 2012, 2 pages, downloaded from http://www.vernay.com/e-commerce/~/media/E-Commerce/Product-PDF/1195-102.pdf.*

*Primary Examiner* — Thomas P Noland
(74) *Attorney, Agent, or Firm* — Patterson Intellectual Property Law, P.C.; Ryan D. Levy

(57) ABSTRACT

A sampling container having a bottle connected to a cap with the cap in communication with a one-way valve for the transport of fluid into the bottle; and the one-way valve configured to receive fluids there through into the opening of the bottle. Further optional embodiments also include a vacuum adapter for attaching the cap to a vacuum pump.

14 Claims, 18 Drawing Sheets

(56) References Cited

U.S. PATENT DOCUMENTS

| | | | |
|---|---|---|---|
| 2009/0100944 A1* | 4/2009 | Newby | 73/864.63 |
| 2009/0215150 A1* | 8/2009 | Kane et al. | 435/243 |
| 2014/0069213 A1* | 3/2014 | Yong | 73/864.63 |
| 2014/0102584 A1* | 4/2014 | Lasnier et al. | 141/18 |

FOREIGN PATENT DOCUMENTS

| | | | | |
|---|---|---|---|---|
| JP | 55006208 A | * | 1/1980 | 73/863.86 |
| JP | 61117429 A | * | 6/1986 | 73/864.63 |
| WO | WO 2006125966 A1 | * | 11/2006 | G01N 1/12 |
| WO | WO 2008130880 A2 | * | 10/2008 | A61J 1/14 |

* cited by examiner

SAMPLING CONTAINER AND METHOD OF SAMPLING

The present application is a nonprovisional of and claims priority to provisional U.S. Patent Application Ser. No. 61/170,610, entitled "Sampling Container and Method of Sampling" filed on Apr. 18, 2009 and provisional U.S. Patent Application Ser. No. 61/239,856, entitled "Improvement on Sampling Container and Method of Sampling" filed on Sep. 4, 2009, the disclosures of which are both incorporated herein by reference.

BACKGROUND OF THE INVENTION

1. Technical Field

The present invention relates to sampling systems which may included containers, pumps, tubing and the like which may provide for an improved sampling of lubricants, fuels, water and various other chemicals. More particularly, the present invention includes a sampling system which provides for minimal contamination of samples while simultaneously reducing the likelihood of environmental contamination.

2. Background Art

Environmental sampling has a long history of use with particular interest of insuring that soil, air or water conditions meet the requirements of the location's specific government entity. For sampling, a variety of different devices are utilized depending upon the nature of the materials to be sampled as well as potential contamination as well as the degree of hazardous of chemicals within the media. Ideally, sampling is in accordance with certain EPA protocols within the United States and furthermore the specific method must be conducted so as to reduce the risk of danger and potential spills in handling a variety of samples.

As a result of the need for meeting EPA protocols, a variety of different sampling methods and apparatuses have been created. For example, in Beausoleil et al., U.S. Pat. No. 5,450,948, a package for transporting temperature-sensitive samples is provided which can be used for ground and water samples that are snugly retained within a cavity of one or more foamed plastic blocks. Furthermore, a liquid absorbent layer is also placed in the bottom of a cooler with the plastic liner bag enclosing the samples within the plastic blocks.

Despite there being a variety of different sampling devices existing in the prior art, there is a need for improved sampling system which may include containers for the sampling of lubricants, fuels, Water and various other chemicals. Furthermore, there is a need for items that include minimal contamination of samples, faster means of sampling, effective configuration control of samples and the reduced likelihood of environmental contamination.

With the prior art, the sampling processes used are prone to contamination of the sample from external sources. The contamination may be caused by ambient dust, contaminated tools, unclean processes, and cross contamination due to multiple use of equipment. There are many techniques used to minimize contamination, but most involve cumbersome steps and additional equipment. Furthermore, the more common techniques involve assembly and disassembly of sampling equipment to adapt to the various types of applications. The required steps increase the likelihood of mistakes and wasted time.

Samples are also subject to loss, mix-incorrect labeling, and data handling mistakes. These mistakes are common in existing processes due to incomplete processes and complex sampling equipment.

Finally, many products on the market are also prone to contamination of the environment. This is especially true when sampling lubricants, fuels, and other chemicals. The causes range from oversampling due to poor quality samples, poor techniques, and disposal of used components.

SUMMARY OF THE INVENTION

The present invention describes a sampling system which improves the effectiveness of sampling lubricants, fuels, water, and various other chemicals. The improvements include minimal contamination of samples, faster means of sampling, effective configuration control of samples, and reduced likelihood of environmental contamination. Additionally, in optional embodiments of the invention, various accessories may be utilized in allowing the system to be used in many different configurations.

The present invention in optional embodiments may provide a means of sampling which is compatible with most sampling points already in existence. This configuration of this optional embodiment provides a "one size fits all" solution to this problem. It also reduces the amount of components necessary to acquire a fluid sample in the field.

In further embodiments, the invention standardizes the processes necessary to encourage configuration control by providing a simple means of sampling equipment identification and sample tracking. Also advantageous is that the invention minimizes the components used to acquire a sample and therefore reduces the disposal of contaminated components. Additionally, optional embodiments of the system provide for different configurations depending upon the sampling needs of the user.

An optional object of the invention is a sampling system, which improves the effectiveness of sampling lubricants, fuels, water and other various chemicals.

Still another optional object of the invention is a sampling system, which provides sampling compatible with most sampling points already in existence.

Another optional object of the invention is a sampling system, which standardizes the processes necessary to encourage configuration control by proving a simple means of sampling equipment identification and sample tracking.

A further optional object of the invention is a sampling system, which minimizes the components used to acquire a sample which may reduce the disposal of contaminated components.

An additional optional object of the invention is a sampling system that includes a vacuum pump for connection to sample bottles.

An additional optional object of the invention is a sampling system that may include an adapter for use with bottles and generic hand vacuum pumps.

An additional optional object of the invention is a sampling system with various accessories for the sampling of fluids.

These aspects and others that have become apparent to the skilled artisan upon review of the following description can be accomplished by providing a sampling system which provides for improved sampling performance. Generally the invention provides for the minimal contamination of samples, faster means of sampling, effective configuration control of the samples and the reduced likelihood of environmental contamination.

It is to be understood that both the foregoing general description and the following detailed description provide embodiments of the invention and are intended to provide an overview or framework of understanding to the nature and character of the invention as it is claimed.

DETAILED DESCRIPTION OF THE PREFERRED EMBODIMENTS

Figure 1:
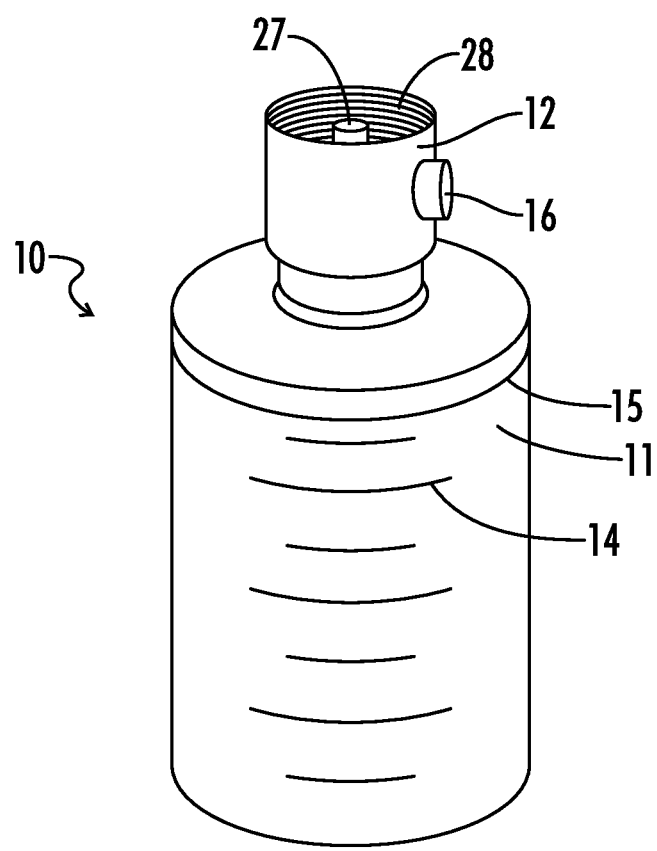
FIG. 1 is an illustration of a perspective view of an embodiment of the sampling container.
Figure 2:
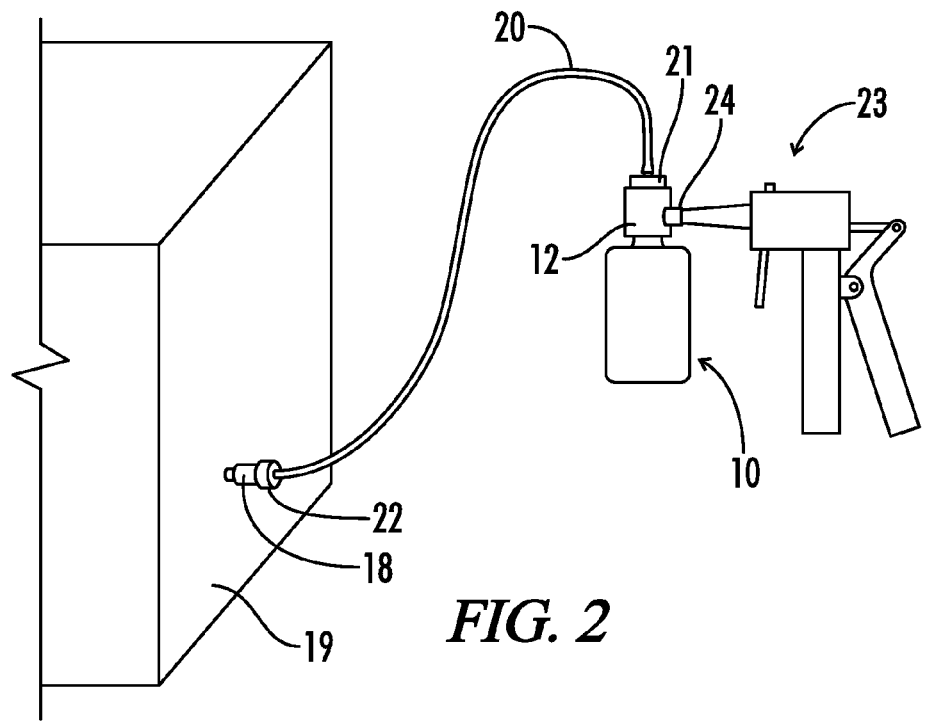
FIG. 2 is an illustration of an application view of an embodiment of the sampling container being used in conjunction with a vacuum pump.
Figure 3:
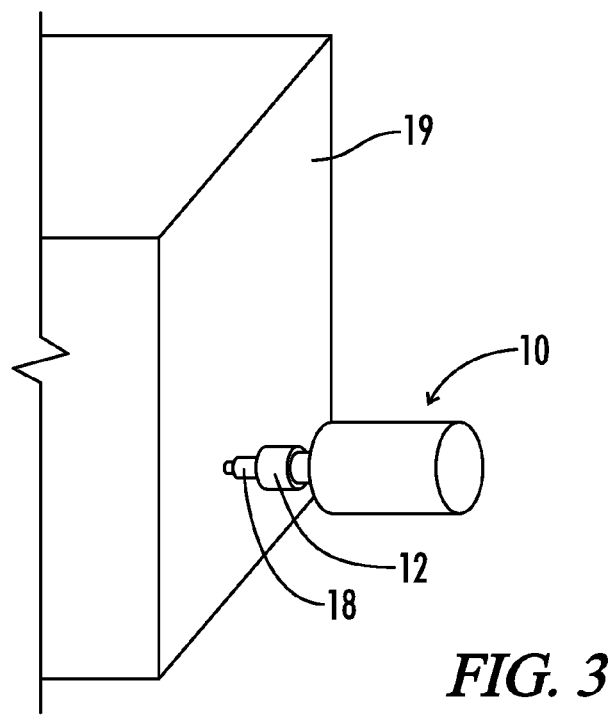
FIG. 3 is an illustration of an application view of an embodiment of the sampling container in use without the vacuum pump.
Figure 4:
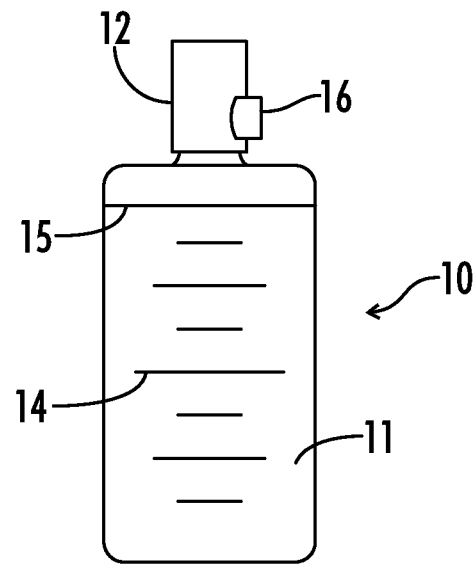
FIG. 4 is an illustration of a side view of an embodiment of the sampling container.
Figure 5:
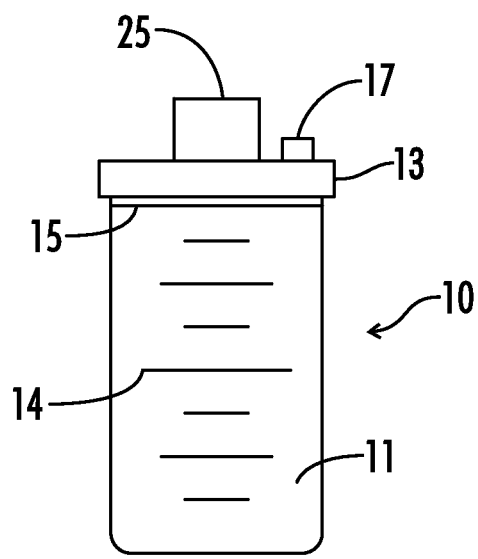
FIG. 5 is an illustration of a side view of an embodiment of the sampling container with an alternate cap design.
Figure 6:
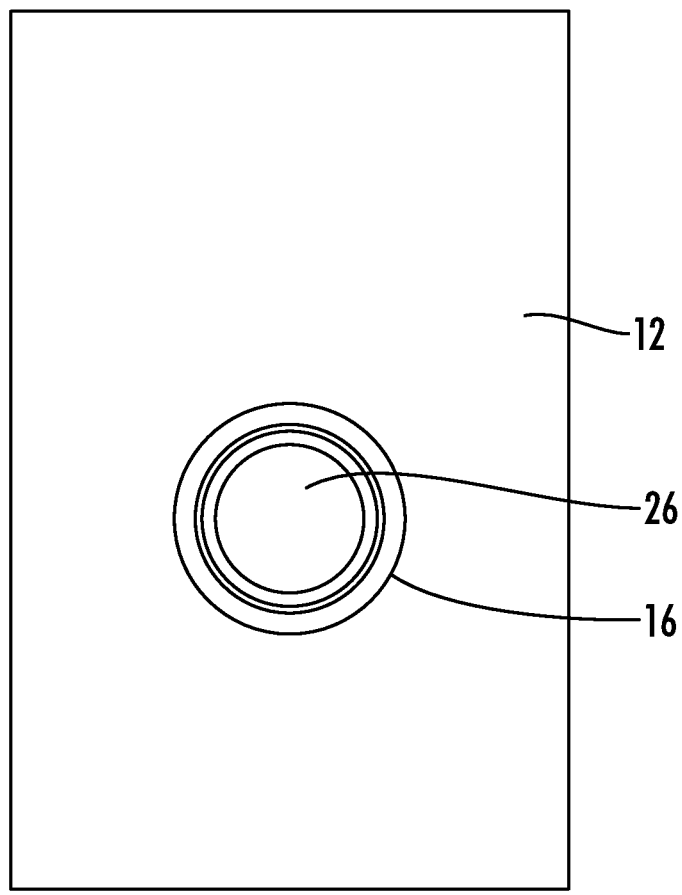
FIG. 6 is an illustration of a side view of an embodiment of the cap.
Figure 7:
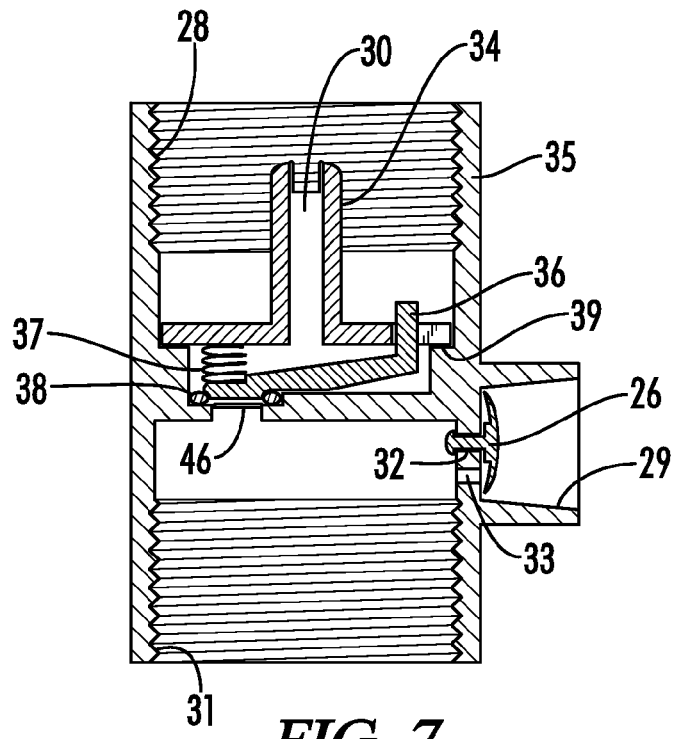
FIG. 7 is an illustration of a sectioned view of an embodiment of the cap with a lever design utilizing a button.

Optional embodiments of the sampling system are illustrated in FIGS. 1-22. In optional embodiments, the sampling system may include sampling container 10. Which may be used to collect samples from reservoirs 19 containing liquids such as lubricants, fuels, Water, and other chemicals. Reservoirs 19 may optionally include gear boxes, gear reducers, storage drums, storage tanks, engine casings and hydraulic tanks. The samples may be taken from sampling ports 18 installed on the reservoirs.

Cap 12 of the sampling container 10 may optionally include a threaded section 28 which allows the sampling container 10 to be connected directly to the sampling ports 18. Sampling ports 18 are generally located in the side of and below the fluid level of a reservoir 19. Sampling ports 18 may be located above or a short distance from the reservoir 19 and connected to the fluid through tubing. Additionally, some sampling ports 18 may be located in the breather adapters at the upper surface of the reservoir 19 (not shown here).

An additional optional embodiment of the sampling container 10 may include have a vacuum placed within the clear bottle 11 when manufactured. This configuration may allow the customer to pull a sample without the need of a vacuum pump 23.

When the sampling container 10 is connected to the sample port 18, the sample tube 27 may open a valve inside the sample port 18 allowing fluid to flow out of the reservoir 19, through the sample port 18, and into the sampling container 10. The sample is contained within the clear bottle 11, and may be measured by means of the level lines 14 on the side of the bottle 11 which are included in optional embodiments. Lines 14 may assist in indicating the ideal fluid level taken during the sampling process. The area above the top line of lines 14 may be left empty to allow for aeration of the sample during transportation and storage. In further embodiments, a variety of different types of lines, notations, symbols and the like may be utilized on bottle 11 so as to provide calibration for a variety of different samples, materials and measurements.

Many applications will allow for the sampling container 10 to be threaded directly to the sampling port 18 as shown in the figures. In some applications, the sample may not flow easily into the sampling container 10. Conditions which may cause this to happen include low reservoir pressure, high sample viscosity, low ambient temperatures, long sample tubes, narrow sample tubes, depleted vacuum charge on sampling container 10 and contaminated samples. In these applications, it may be necessary to optional embodiments of the invention which may include vacuum pump 23 to assist in pulling the sample.

In optional arrangements, vacuum pump 23 may connect to the vacuum port 16 on the cap as shown at location 24. In optional embodiments, vacuum pump 23 may be used in combination with an extension tube 20.

In additional optional embodiments, vacuum pump 23 may include a construction so as to provide a user with the capacity to manually release pressure. This release may allow the operator to prevent the vacuum pump 23 from pulling sample fluid out of the sampling container 10 and into the vacuum pump 23.

When using a vacuum pump 23 or using an extension tube 20, optional embodiments may provide for adapters 21 and 22 to make the connection necessary for the pump. In certain embodiments, cap adapter 21 may connect to cap 12 to the extension tubing 20. Additionally, sample port adapter 22 may connect the extension tube 20 into sampling port 18.

In optional embodiments, multiple cap 12 configurations exist for the present invention. One optional embodiment connects to a bottle which has a port 29 which may contain threading. Vacuum port 16 may optionally located on the side of the cap 12. Alternatively, cap 13 may be used for bottles which have a large threaded connection. In optional embodiments, alternate vacuum port 17 may located on the horizontal surface of the cap 13. The connection 25 is similar to the connection on cap 12.

Cap 12 side may optionally include vacuum port 16 with umbrella valve 26. Umbrella valve 26 may be understood to be a one way valve often formed of rubber, polymer or the like. In further optional embodiments, additional one-way valves may be utilized.

In describing the multiple optional embodiments of cap 12, each optional embodiment may include different configurations and a different internal mechanism. No limitation is intended by only describing some features with certain optional embodiments.

Embodiments of cap 12 may attach and seal with threads 31. The caps may seal and maintain a vacuum on bottle 11. Additionally, optional embodiments of the cap are for adapting to all common sample port 18 fittings. Yet further, the various cap configurations help to function in reliably pull samples from sample port 18 when connected. Cap 12 advantageously maintains a normally closed valve before taking a sample. Once cap 12 is connected to the sample port 18 or cap adapter 21, it is in the open position or has the ability to open (manual operation) the valve and allow sample fluid to pass through.

Optional embodiments of cap 12 may be a lever cap 35 which may include a lever design with a button to open the valve. The sample tube 34 can fit and seal inside the sample port 18. Sample tube 34 may rest and be secured against cap surface 39.

When lever cap 35 is threaded onto the sample port 18 through use of threads 28 (though in optional embodiments may not include threads), lever 36 may be pushed back at the button like surface. This action pulls the other end of the lever 36 away from the o-ring 38 seal and compress the spring 37. As such, there can be fluid communication between the sample tube 34 and the valve bore 46. The sample tube 34 opens the internal valve in the sample port 18 when in compression. This action may allow sample fluid to flow through the sample tube bore 30, past the o-ring 38 seal, through the valve bore 46, and into the bottle 11. The lever cap 35 may then be unscrewed from the sample port 18 to close the valve. The spring 38 maintains the valve closed while in storage.

In further optional embodiments, vacuum pump 23 may be used to assist in pulling the sample into the bottle 11. Vacuum pump 23 connects to the cap 35 at side surface 29. The umbrella valve 26 can allow air to be pulled from the bottle 11 through the umbrella valve vent 33. Umbrella valve 26 can be secured at the umbrella valve connection 32. Air cannot substantially return into the bottle 11 through the umbrella valve vent 33 due to the one way design of umbrella valve 26. Vacuum pump 23 may also be used to draw a vacuum on the sampling container 10 prior to use.

Figure 8:
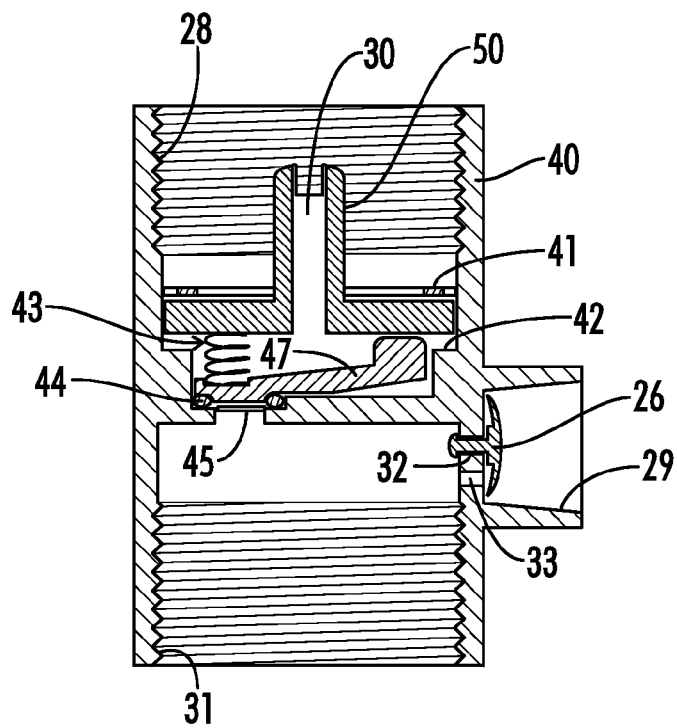
FIG. 8 is an illustration of a sectioned view of an embodiment of the cap with a lever design utilizing a sliding sample tube.
Figure 9:
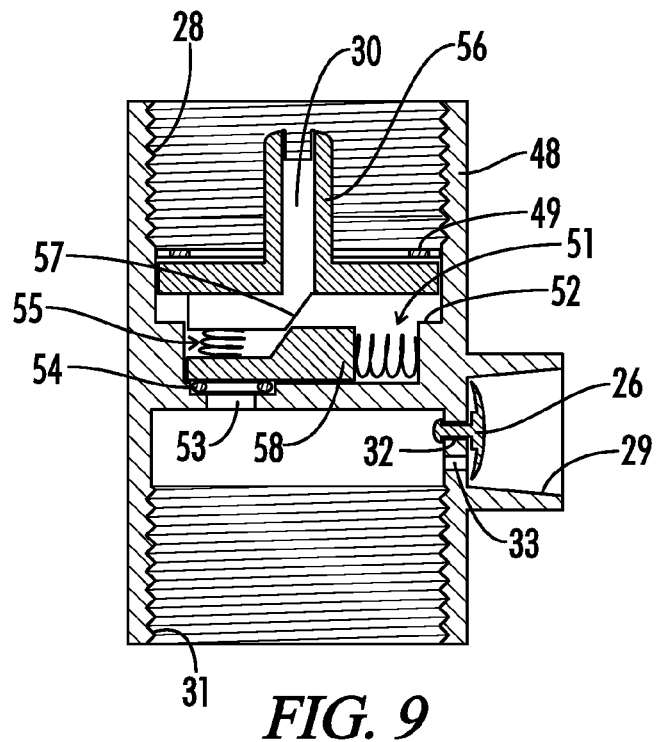
FIG. 9 is an illustration of a sectioned view of an embodiment of the cap with a sliding valve design.
Figure 10:
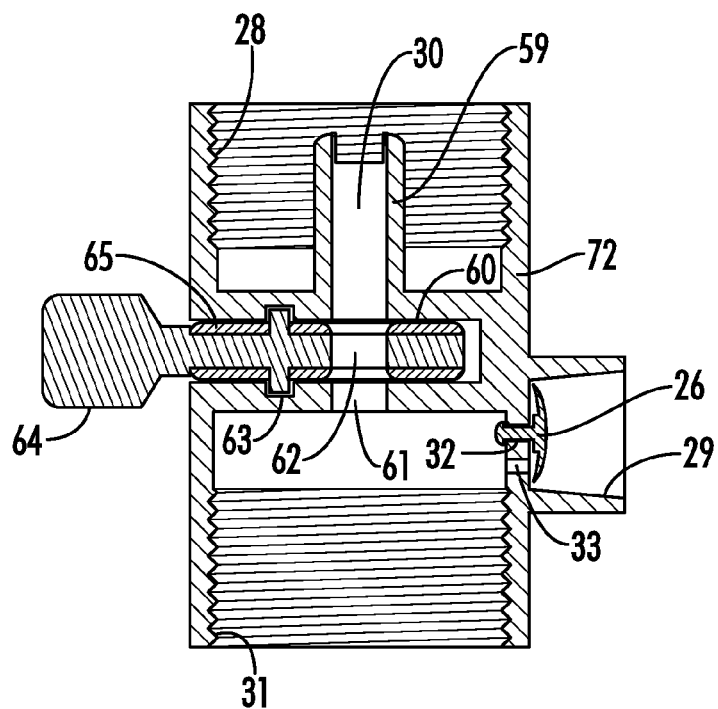
FIG. 10 is an illustration of a sectioned view of an embodiment of the cap with a rotating valve design
Figure 11:
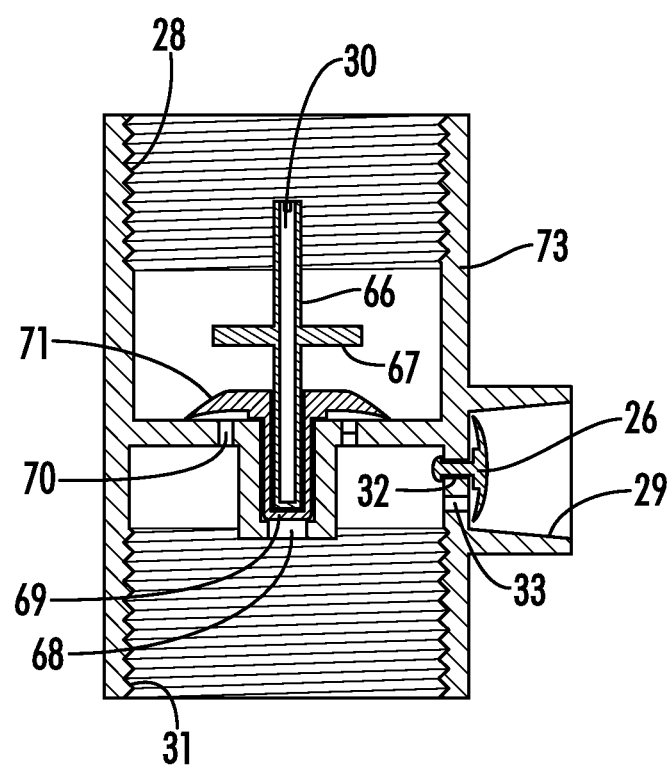
FIG. 11 is an illustration of a sectioned view of an embodiment of the cap with a piercing sample tube design.
Figure 12:
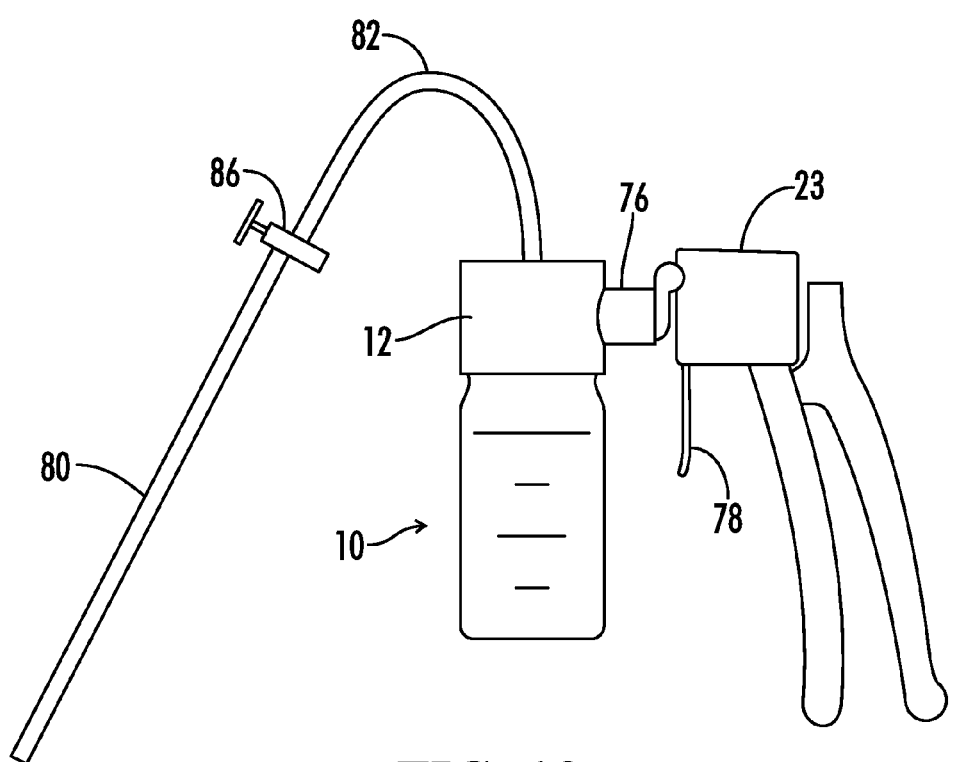
FIG. 12 is an illustration of an embodiment of the sampling container in communication with a vacuum pump and a valve.
Figure 13A:
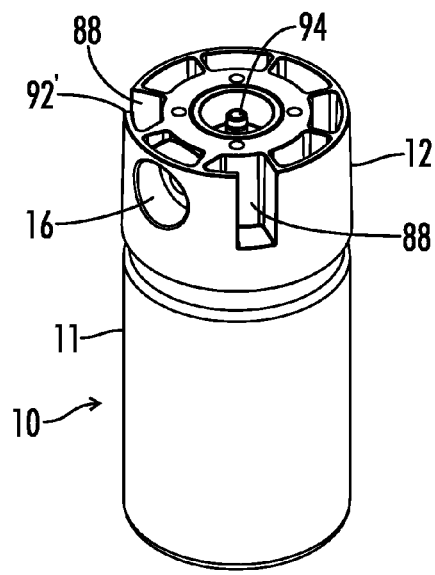
FIGS. 13a-c are illustrations of further embodiments of cap connected to a bottle of a sampling container.
Figure 13B:
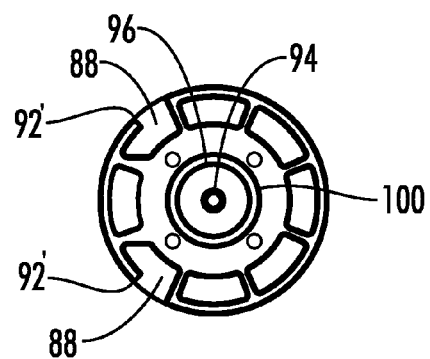
Figure 13C:
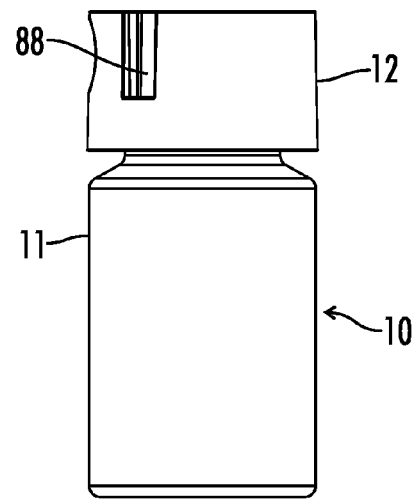
Figure 14A:
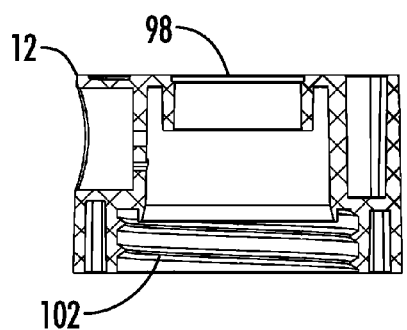
FIGS. 14a-d are illustrations of embodiments of cap of a sampling container.
Figure 14B:
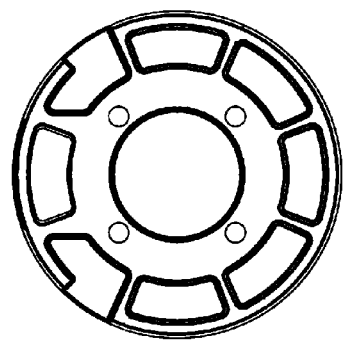
Figure 14C:
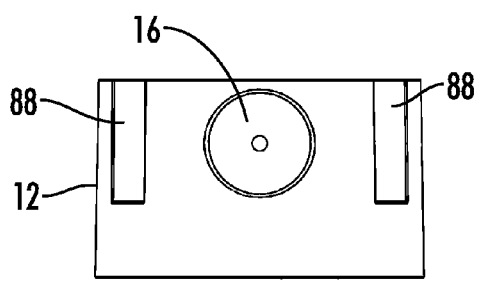
Figure 14D:
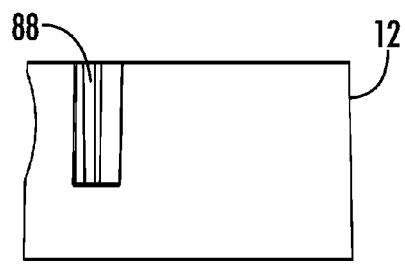
Figure 15:
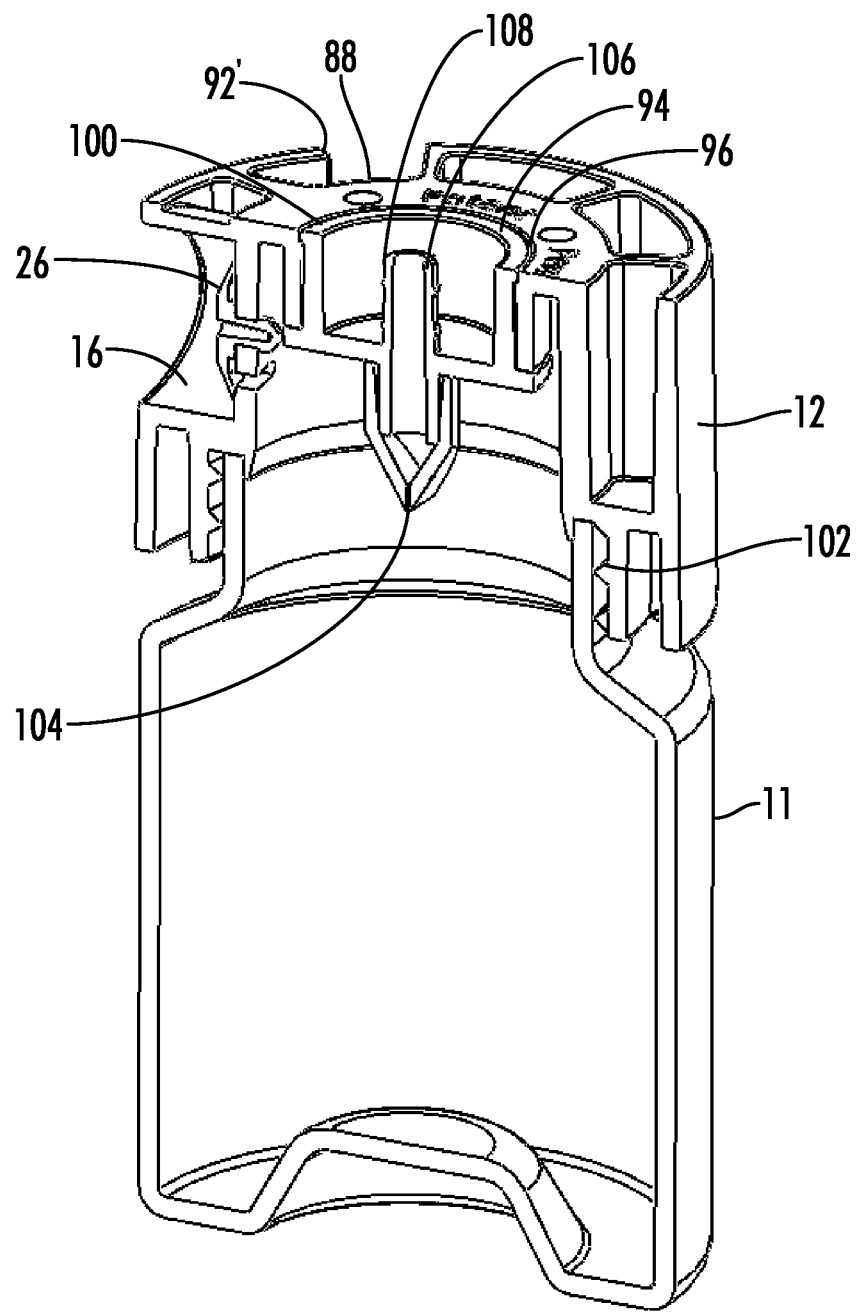
FIG. 15 is a cross-sectional view of a further embodiment of a sampling container.
Figure 16:
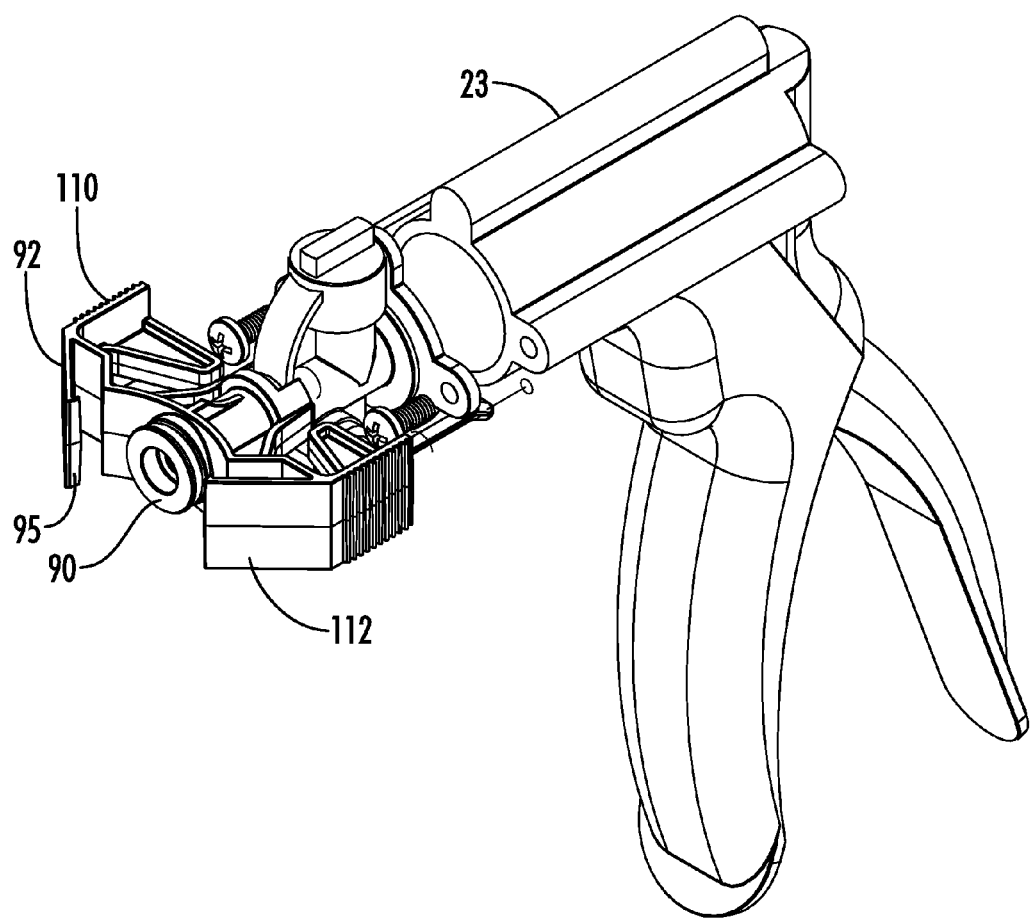
FIG. 16 is a view of an embodiment of the vacuum pump adapter with vacuum pump.
Figure 17:
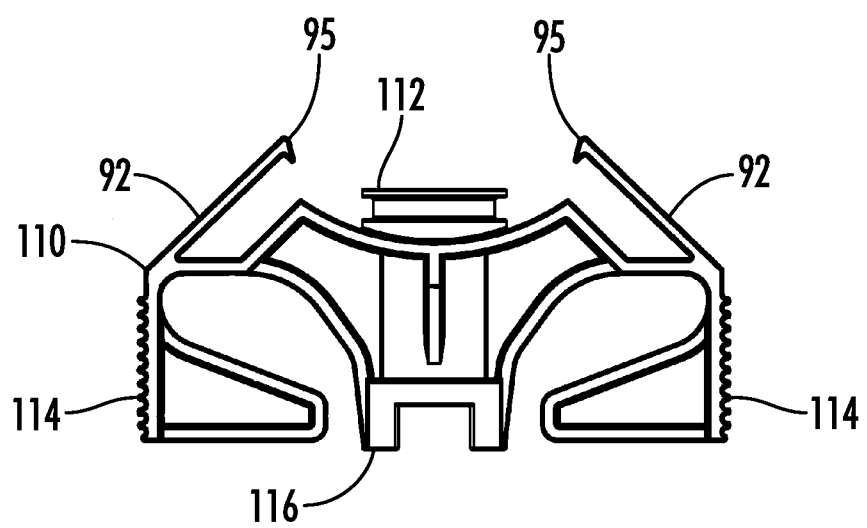
FIG. 17 is a view of an embodiment of the vacuum pump adapter.
Figure 18:
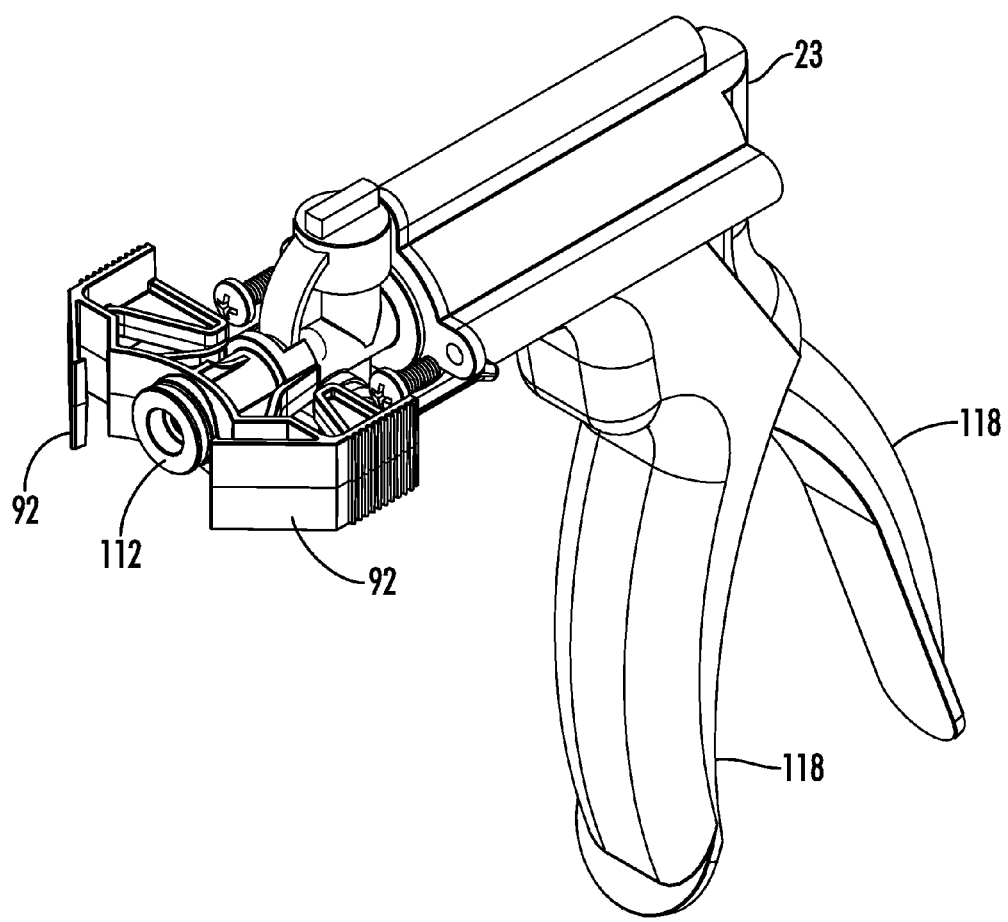
FIG. 18 is a view of an embodiment of the vacuum pump adapter attached to the vacuum pump.
Figure 19:
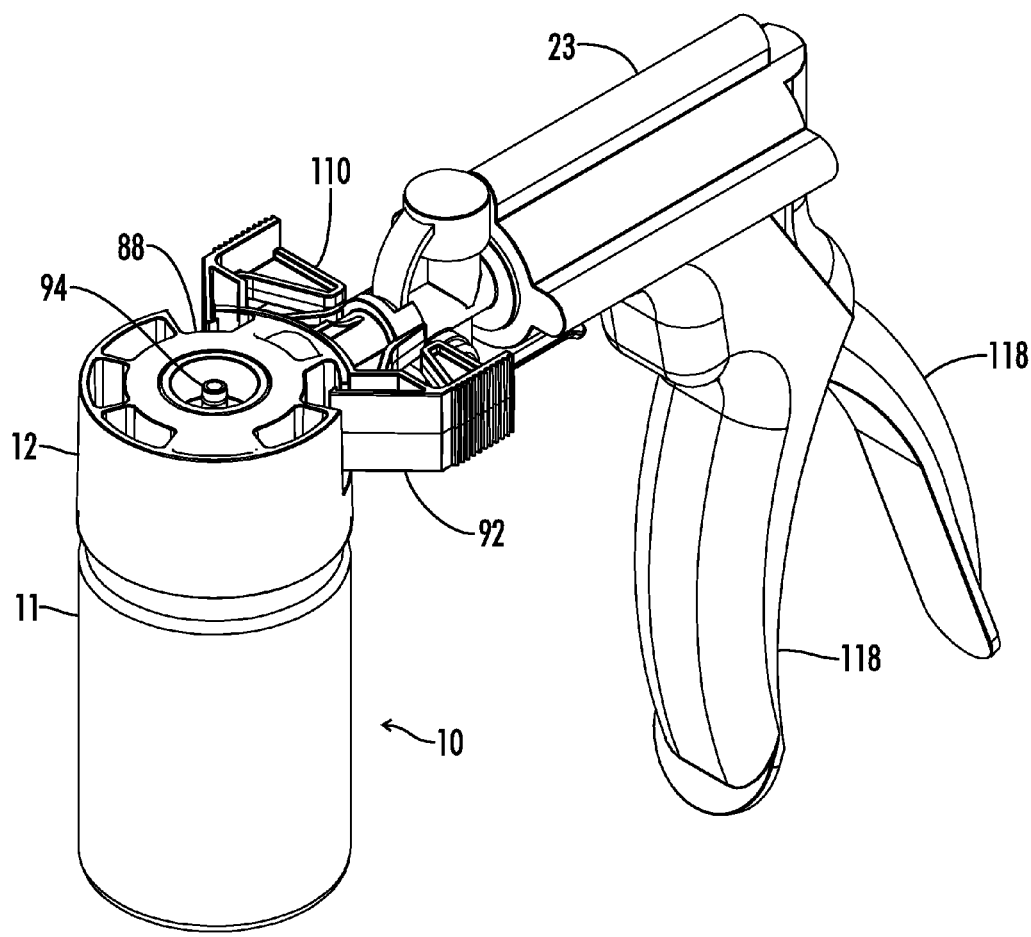
FIG. 19 is a view of an embodiment of the vacuum pump with adapter engaged with the cap and bottle.
Figure 20:
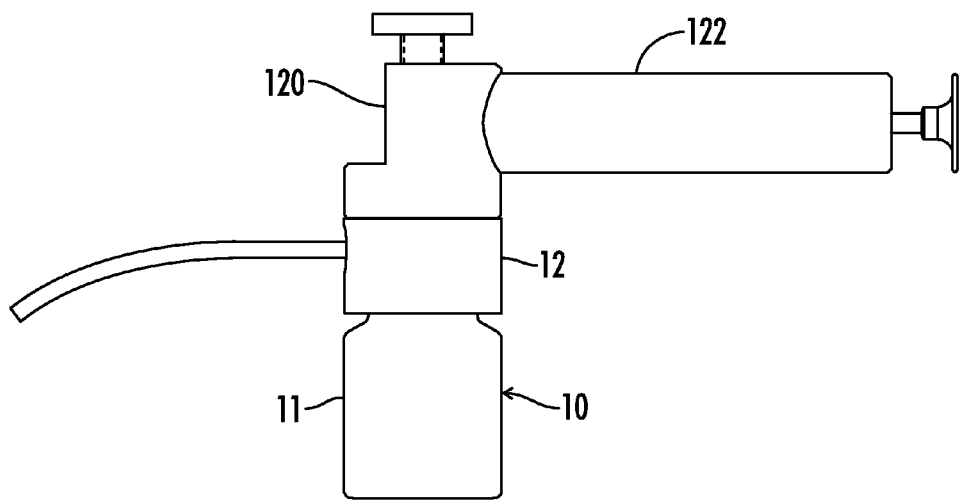
FIG. 20 is a view of an embodiment of the vampire adapter and vampire sampler in communication with a cap and bottle.
Figure 21A:
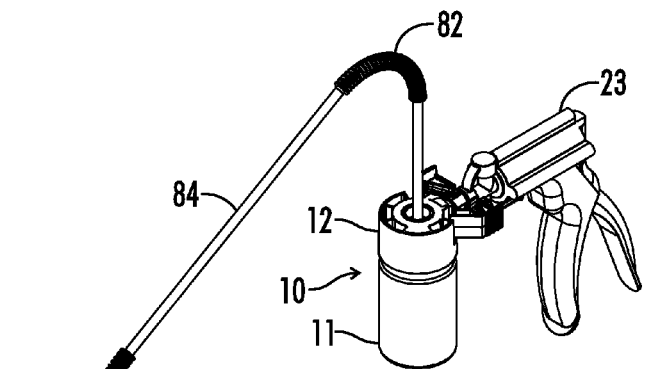
FIG. 21a-b are views of embodiments of the vacuum pump with adapter connected to a cap and bottle with tubing.
Figure 21B:
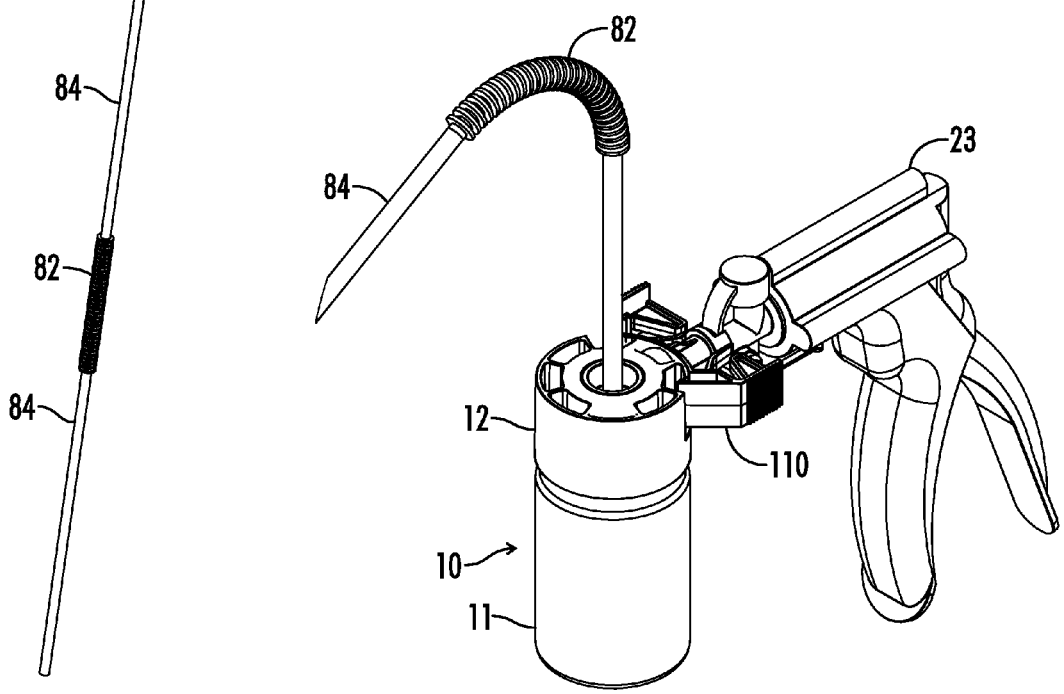
Figure 22:
FIG. 22 is a view of an embodiment of tubing having corrugated and non-corrugated sections.

In looking at section view 40 as indicated in FIG. 8, a sectional view of cap 12 in an optional embodiment as sliding cap 40 which utilizes a lever with a sliding sample tube 50 to open the valve. The sample tube 50 can fit and seal inside the sample port 18 once it has been pushed against the shelf 42. A retaining ring 41 limits the sample tube 50 from moving in the direction opposite the shelf.

When the cap 40 threads onto the sample port 18 by threads 28, the sampling tube 50 is pushed against the shelf 42. This action pushes the lever 47 back at the button like surface. The other end of the lever 47 can move away from the o-ring 44 seal and compress the spring 43. This action provides for fluid communication between the sample tube 50 and the valve bore 45. The sample tube 50 can open the internal valve in the sample port 18 when in compression. This action can allow sample fluid to flow through the sample tube bore 30, past the o-ring 44 seal, through the valve bore 45, and into the bottle 11. The cap 40 can then be unscrewed from the sample port 18 to close the valve. The spring 43 maintains the valve closed while in storage.

In further optional embodiments, a vacuum pump 23 may be used to assist in pulling the sample into the bottle 11. Vacuum pump 23 may connect to the cap 40 at the side surface 29. Umbrella valve 26 may allow air to be pulled from the bottle 11 through the umbrella valve vent 33. The umbrella valve 26 can be secured at the umbrella valve connection 32. Air cannot substantially return into the bottle 11 through the umbrella valve vent 33 due to the one way design of the umbrella valve 26. The vacuum pump 23 may also be used to draw a vacuum on the sampling container 10 prior to use.

In further optional embodiments of cap 12, sliding valve cap 48 may use a sliding valve design with a sliding sample tube 56 to open the valve. The sample tube 56 may fit and seal inside the sample port 18 once it has been pushed against the shelf 52. A retaining ring 49 limits the sample tube 56 from moving in the direction opposite the shelf 52.

When the sliding valve cap 48 threads onto the sample port 18 by threads 28 though not in all embodiments, sampling tube 56 may be pushed against the shelf 52. This action may push slider 58 to the side by a sliding contact with the tapered surface 57. The other end of the lever 58 can move away from the o-ring 54 seal and spring 55. This action can allow fluid communication between the sample tube 56 and the valve bore 53. The sample tube 56 can open the internal valve in the sample port 18 when in compression. This action can allow sample fluid to flow through the sample tube bore 30, past the o-ring seal 54, through the valve bore 53, and into the bottle 11. Sliding valve cap 48 can then be unscrewed from the sample port 18 to close the valve. The spring 51 can maintain the valve closed while in storage.

Additionally, in further optional embodiments, there may be both a cap and adapter used with obtaining a fluid sample. In optional embodiments, an adapter could fit between the could fit between the bottle and the bottle cap for storage and shipping. The bottle cap could be removed when attaching the adapter/bottle to the pump, and then the cap would be replaced for shipping. Other ports and or plugs may be utilized for attaching to the pump and what not in obtaining a substantially airtight seal.

In further optional embodiments, vacuum pump 23 may be used to assist in pulling the sample into the bottle 11. The vacuum pump 23 can connect to cap 48 at the side surface 29. Umbrella valve 26 can allow air to be pulled from the bottle 11 through umbrella valve vent 33. Umbrella valve 26 can be secured at the umbrella valve connection 32. Air cannot substantially return into the bottle 11 through umbrella valve vent 33 due to the one way design of umbrella valve 26.

In further optional embodiments, cap 12 may be a rotating valve cap 72 which utilizes a rotating valve design to open the valve with a fixed sample tube 59. Sample tube 59 can fit and seal inside the sample port 18 once cap 72 has been connected to the sample port 18. Pivot point 63 can secure the rotating device 64. Gasket 65 may be secured to both sides of the rotating device 64 and seals at contact surfaces 60. Gasket 65 can maintain a seal on the sampling container 10 while not in use.

When the rotating valve cap 72 threads onto the sample port 18 by threads 28, the operator move rotating device 64. This action allows fluid communication between the sample tube 59 and the valve bore 61. The sample tube 59 can open the internal valve in the sample port 18 when in compression. This action can allow sample fluid to flow through the sample tube bore 30, through the rotating valve bore 62, through the valve bore 61, and into the bottle 11. The operator can then close rotating valve 64 when the bottle 11 is full. Cap 72 can then be unscrewed from the sample port 18.

Similarly to the other optional embodiments, a vacuum pump 23 may be used to assist in pulling the sample into the bottle 11. Vacuum pump 23 can connect to the cap 72 at the side surface 29. Umbrella valve 26 allows air to be pulled from bottle 11 through umbrella valve vent 33. Umbrella valve 26 can be secured at the umbrella valve connection 32. Air cannot substantially return into the bottle 11 through the umbrella valve vent 33 due to the one way design of umbrella valve 26. Vacuum pump 23 may also be used to draw a vacuum on sampling container 10 prior to use.

In further optional embodiments, cap 12 may be a piercing cap which utilizes a piercing sample tube design to puncture diaphragm 69 and open a connection to the bottle 11. Sample tube 66 can fit and seal inside the sample port 18 once cap 73 has been connected to the sample port 18. Surface 67 pushes against the umbrella valve 71 when connected. Surface 67 can prevent the sample tube 66 from traveling beyond its intended design. Umbrella valve 71 can secure the sample tube 66 before and throughout the life of the product.

Cap 73 can threaded onto the sample port 18 by threads 28, the sample tube 66 can puncture the diaphragm 69. This action can allow fluid communication between the sample tube 66 and the valve bore 68. Sample tube 66 can open the internal valve in the sample port 18 when in compression. This action can allow sample fluid to flow through the sample tube bore 30, through the valve bore 68, and into the bottle 11. When the sample is taken, cap 73 can then be unscrewed from the sample port 18.

Optionally, vacuum pump 23 may be used to assist in pulling the sample into the bottle 11. The vacuum pump 23 can connect to piercing cap 73 at side surface 29. Umbrella valve 26 can allow air to be pulled from bottle 11 through umbrella valve vent 33. Umbrella valve 26 can be secured at umbrella valve connection 32. Air cannot substantially return into bottle 11 through umbrella valve vent 33 due to the one way design of umbrella valve 26. Vacuum pump 23 may also be used to draw a vacuum on sampling container 10 prior to use.

Air may be removed from the sampling container 11 through the open cap end at the threads 28. Furthermore, in optional embodiments, an adapter may be connected between cap threads 28 and cap adapter 21. This adapter may be used to connect the vacuum pump 23 or other equipment.

In further optional embodiments, vacuum pump 23 may be attached to bottle cap 12 in various constructions including but not limited to mechanical fastening mechanisms, threaded interfaces, magnetic forces, vacuum forces, or by chemical bonds. Interface 76 provides a sealed connection whereby the vacuum created inside the vacuum pump 23 is in fluid communication with bottle cap 12 and therefore sampling container 10. A one way check valve may be placed inside bottle cap 12 therefore limiting the fluid communication of vacuum pump 23 and the sampling container 10.

Interface 76 may serve to create a vacuum inside the bottle. It also can serve the purpose of supporting sampling container 10 while a sample is taken. The operator can maintain the sampling container 10 in a vertical orientation while operating the vacuum pump 23. This task can be accomplished with one hand. Another reason for the interface 76 is that when it is used with an internal check valve it provides a connection which does not introduce contaminants into the sampling container 4 and therefore the sample Vacuum pump 23 may also include relief lever 78 which neutralizes the vacuum inside the pump when actuated by the operator. Relief lever 78 provides an advantage in that it helps to prevent overfilling of the sampling container 10, drawing fluid into the vacuum pump, and wasteful oversampling.

Sampling probe 80 includes a rigid tube 84 which is immersed into the fluid. One or more flexible tubes 82 connect the rigid tube 84 to the sampling container 10 or connect multiple rigid tubes 84 together. In optional embodiments, sample fluid is drawn through the rigid tube 84 and flexible tube 83 into the sampling container 10. Flexible tube 82 may allow for the maneuvering of the rigid tube 84 while maintaining the sampling container 10 in a vertical orientation. The rigid tube 84 and flexible tube 82 may be joined together during assembly or may be fabricated as one part.

Further optional embodiments of the invention may include manual valve 86 located between the flexible tube 82 and the sampling container 10 or the rigid tube 84 and the flexible tube 82. This normally closed manual valve 86 allows the operator to start and stop the sampling process and to control the rate of flow during sampling. Manual valve 86 may optionally be used when using a pre-charged sampling container 10 with the sampling probe 80, because it may allow the operator to begin drawing a sample after the flexible tube 82 is connected to the sampling container 10 and the rigid tube 84 immersed in the fluid.

In further optional embodiments of the invention, cap 12 may include pump channels 88 for connecting vacuum pump 23 to sampling container 10. Generally, pump channels 88 may be on both sides of vacuum port 29 and serve to maintain pump connection with cap 12. In optional embodiments, pump channels 88 may include a somewhat hooked outer surface 92' for better holding onto the corresponding vacuum pump wings 92 of vacuum pump 23. Generally, pump channels 88 may be molded into cap 12 and further provide for a mechanical engagement of the vacuum pump to the cap.

In optional embodiments of cap 12, cap 12 may include one-way valve 94 within cap 12. One-way valve 94 may be removably placeable within cap 12 or in further embodiments may be fixed within cap 12. In further optional embodiments of the invention one way valve 94 may be of a variety of valves that function in one way from a variety of different check valves to diaphragm valves to the different types of valves as used throughout the application. In further optional embodiments, cap 12 may include a variety of surrounding surfaces 96 about valve 96 as threading, smooth, or alternatively ridged or the like may be utilized with the invention. In further optional embodiments, cap 12 may include closed surface 98 so as to not include a valve at all. In such optional embodiments, the vacuum port could be used for both for the transfer of fluids or alternatively the closed style could be used simply to maintain a sterile environment or control for the user. Generally, one-way valve 94 fits within valve position 100 on the top of cap 12 in the middle of surrounding surfaces 96. Optionally, valve 94 may be relocated depending on the needs of the user. Additionally, in further optional embodiments, a variety of different strength valves may be utilized as the fluids for testing may vary from water, to a fluid with a high viscosity. In many optional embodiments, cap 12 will also have bottle threads 102 so in such embodiments of cap 12, cap 12 can connect and fit upon bottle 11.

In optional embodiments of one way valve 94, one way valve 94 may include flow control element 104, which may include portions of the valve that may open or close depending on the direction of the flow of fluid. Generally, the one-way valve functions so as to allow fluid into bottle 11 but not out of bottle 11. In further optional embodiments, one way valve 94 includes nipple 106 for connecting to tubing or the like for the sampling of fluids. Nipple 106 may also include ridges 108 which may be assist in the connecting of tubing there to for sampling.

In yet further optional embodiments, a one way valve may not be included for the control of the fluid, rather their might be a nipple or tube available for fluid input into the bottle. In such embodiments, a user may cap the bottle thereafter to preclude the discharge of fluid from the bottle. Generally, a similar arrangement can be provided as the embodiments with a one-way valve embodying a duck valve, though the conduit is open without any flaps to arrest the flow of fluid. In such embodiments, the vacuum pump may still be employed in creating a pressure difference to influence fluid into the bottle.

In further optional embodiments, vacuum adapter 110 may include connection wings 92 with catches 95 for attaching to the channels 88 of cap 12. In such optional embodiments, wings 92 may flex to fit within channels 88 to connection vacuum pump 23 to cap 12 of sampling container 10. Though the fit of wings 99 within channels 88, vacuum pump 23 may be in a configuration so as to pull a vacuum upon bottle 11. Generally, vacuum pump engagement 112 is pulled in close contact with vacuum port 16 of cap 12 and thus a user may pull a vacuum on the bottle. In further optional embodiments, washers or the like may be used at the vacuum pump engagement 112 so that a user maintains an improved seal upon the cap.

In further optional embodiments, vacuum adapter 110 may be understood to be a stand-alone piece that may be sold to retrofit existing vacuum pumps. In such embodiments, a user may simply attach the vacuum adapter to a preexisting vacuum pump and be ready to engage caps with the vacuum adapter. In optional embodiments, vacuum adapter includes grasps 114 so that a user may flex wings 92 so that they may fit within channels 88 of cap 12. Vacuum adapter 110 may also include pump side 116 which connects to the body of the vacuum pump.

In further optional embodiments, vacuum adapter 110 is integrated alternatively permanently attached to vacuum pump 23. In practice, a user would push together handles 118 to pull a vacuum with vacuum pump 23. In further optional embodiments, a variety of different pumps may be used and the invention is not limited to one such form. Additionally, vacuum adapter 110 may also be of a configuration to fit with a variety of other designs of vacuum pumps.

In yet further optional embodiments, the invention may include plunger adapter 120. Plunger adapter 120 may allow for the connection of plunger 122 so that a user may pull on the bottle and thus create a vacuum. Generally, plunger 122, upon each pull, creates a pressure differential that can influence fluid into the bottle. Again, this may be accomplished without opening cap 12. In such optional embodiments, a user may connect plunger 122 and further connect to a fluid tube and thus pull fluid into the bottle.

In yet further optional embodiments of the invention, the flexible tube 82 may comprise corrugated sections that can bend and thus allow the user to draw samples through a tube that bends and can fit to the area of the fluid. As can be the case, a user can thus then remove fluid from the bottom of the reservoir or drum, or from a more distant location due to the combination of the corrugated section and non-corrugated sections of the tube.

In further optional embodiments a tube may have an inner diameter of 3/16 inches and about 48 inches in length. Generally, the tubing may include three sections of non-corrugated tubing of about 9 inches each and about three sections of corrugated tubing of about four inches each. In further optional embodiments the tubing may be translucent or transparent. Yet in additional optional embodiments, each section of tubing is separate yet can lock together to form a continuous conduit for fluid. This may include three separate nine inch sections and three separate corrugated sections.

In practice of the present invention, a user can extract samples without ever having to remove the cap from the bottle. Advantageously, such designs can be used for a variety of different fluids as the caps have the capacity to have vacuum applied. In optional methods, a user may supply the caps already with a vacuum within the bottle. Thus, an operator in the field would simply have to connect the bottle to pull the sample. In further optional embodiments, a user applies an additional vacuum to the bottle so that fluid is drawn within by either a hand pump or the like through the ports available on the cap. As such, the possibility of contamination is decreased.

Yet furthermore, through the use of the novel vacuum pump adapter, a user can retrofit a hand pump so that the caps with channels can be used to provide for a fit between the vacuum pump and the bottle. The use of one-way valves within the cap further provides for a lesser likelihood of fluid escaping from the bottle as well as provides a decrease in the chances of contamination of the fluid.

In further optional embodiments, one-way valves are used so as to be able to provide a user with the attachment for tubes which can correspond to the inner diameter of tubing for transport of the fluid.

Thus optional embodiments of the invention provide for both a pre-charged sampling container, having a vacuum as well as for sampling containers without a vacuum though that can indeed have a vacuum pulled there upon by a vacuum pump.

Finally, as used herein "vacuum" is defined to mean a pressure difference between the interior of the bottle and the surrounding atmosphere so as to draw fluid into the vacuum. One should not take the use of vacuum within this application to mean that the interior of the bottle is free from matter, rather the pressure is less inside the bottle thus causing fluids to flow into the bottle.

The above description is intended to enable the person skilled in the art to practice the invention. It is not intended to detail all the possible variations and modifications that are apparent to the skilled worker upon reading the description. It is intended, however, that all such modifications and variations be included within the scope of the invention that is defined by the following claims. The claims are intended to cover the intended elements and steps that any arrangement or sequence that are effective to meet the objectives and intended for the invention, unless the context specifically indicates to the contrary.

What is claimed is:

1. A sampling container comprising:
   a bottle connected to a cap;
   the cap in communication with a one-way valve for the transport of fluid into the bottle, the one-way valve only opens when the cap is connected to a sampling port and closes when the cap is disconnected from the sampling port; and
   the one-way valve configured to receive fluids there through into the opening of the bottle.

2. The sampling container of claim 1 further comprising a vacuum port for the attachment of a vacuum pump.

3. The sampling container of claim 2 wherein the vacuum port comprises a one-way valve.

4. The sampling container of claim 3 wherein the one-way valve comprises an umbrella valve.

5. The sampling container of claim 1 wherein the cap comprises pump channels.

6. The sampling container of claim 1 wherein the one-way valve comprises a nipple for connecting to tubing for the fluid.

7. The sampling container of claim 1 wherein the one-way valve comprises an opening and a non-permanently closed end that opens to allow fluid within the bottle.

8. The sampling container of claim 1 wherein the bottle comprises indication lines for measuring the amount of fluid.

9. The sampling container of claim 1 wherein adapters may be connected to the cap to sample from differently designed ports.

10. The sampling container of claim 1 wherein the cap comprises threads for connecting to the sampling port.

11. The sampling container of claim 1 wherein the cap comprises a lever cap with a lever to open the one-way valve when the cap is connected to the sample port.

12. The sampling container of claim 1 wherein the cap comprises a sliding cap with a lever to slide and open the one-way valve when the cap is connected to the sample port.

13. The sampling container of claim 1 wherein the cap comprises a rotating valve cap with a rotating valve design to open the one-way valve when the cap is connected to the sample port.

14. The sampling container of claim 1 wherein the cap comprises a piercing valve cap to puncture a diaphragm and open the one-way valve when the cap is connected to the sample port.

\* \* \* \* \*